(12) United States Patent
Kim et al.

(10) Patent No.: US 9,303,261 B2
(45) Date of Patent: Apr. 5, 2016

(54) COMPOSITION FOR CONTROLLING CHROMOGENESIS INCLUDING MICRORNA

(75) Inventors: Kyu Han Kim, Yongin-si (KR); Hyun Jung Choi, Yongin-si (KR); Bum Ho Bin, Yongin-si (KR); Tae Ryong Lee, Yongin-si (KR)

(73) Assignee: Amorepacific Corporation, Seoul (KR)

( * ) Notice: Subject to any disclaimer, the term of this patent is extended or adjusted under 35 U.S.C. 154(b) by 64 days.

(21) Appl. No.: 14/126,505

(22) PCT Filed: Jun. 13, 2012

(86) PCT No.: PCT/KR2012/004645
§ 371 (c)(1),
(2), (4) Date: Dec. 16, 2013

(87) PCT Pub. No.: WO2012/177008
PCT Pub. Date: Dec. 27, 2012

(65) Prior Publication Data
US 2014/0134636 A1    May 15, 2014

(30) Foreign Application Priority Data

Jun. 23, 2011  (KR) .................. 10-2011-0061107

(51) Int. Cl.
| | | |
|---|---|---|
| *C12N 15/113* | (2010.01) | |
| *A61K 31/7105* | (2006.01) | |
| *A61K 8/00* | (2006.01) | |
| *A61K 8/60* | (2006.01) | |
| *A61Q 5/10* | (2006.01) | |
| *G01N 33/50* | (2006.01) | |

(52) U.S. Cl.
CPC ............ *C12N 15/1137* (2013.01); *A61K 8/606* (2013.01); *A61K 31/7105* (2013.01); *A61Q 5/10* (2013.01); *C12N 15/113* (2013.01); *G01N 33/5023* (2013.01); *A61K 2800/78* (2013.01); *A61K 2800/782* (2013.01); *C12N 2310/113* (2013.01); *C12N 2310/141* (2013.01)

(58) Field of Classification Search
USPC ............ 435/6.1, 91.1, 91.31, 455, 6.11, 6.13, 435/375; 514/44; 536/23.1, 24.3, 24.5, 24.4
See application file for complete search history.

(56) References Cited

U.S. PATENT DOCUMENTS

| | | | | |
|---|---|---|---|---|
| 7,232,806 | B2 * | 6/2007 | Tuschl et al. ................ | 514/44 A |
| 7,504,385 | B2 | 3/2009 | Binetti et al. | |
| 7,635,563 | B2 * | 12/2009 | Horvitz et al. ............... | 435/6.11 |
| 2009/0010908 | A1 * | 1/2009 | Gow et al. .................... | 424/94.1 |
| 2011/0143948 | A1 | 6/2011 | Perera | |

FOREIGN PATENT DOCUMENTS

KR    10-2011-0068061 A    6/2011

OTHER PUBLICATIONS

Holst et al., Experimental Dermatology, vol. 20, pp. 278-296 (2010)).*
David TS Wu, et al., "Mir-434-5p mediates skin whitening and lighting", Clin Cosmet Investing Dermatol, 2008, pp. 19-35, vol. 1.
Z. Zhu, et al., "MicroRNA-25 functions in regulation of pigmentation by targeting the transcription factor MITF in alpaca (*Lama pacos*) skin melanocytes", Domestic Animal Endocrinology, 2010, pp. 200-209, vol. 38.

* cited by examiner

Primary Examiner — Jane Zara
(74) Attorney, Agent, or Firm — Sughrue Mion, PLLC (57) ABSTRACT

Disclosed is a composition for a whitening effect or for the prevention of gray hair, which includes antisense nucleic acid molecules of SEQ ID NO: 2, wherein the composition has an miRNA of SEQ ID NO: 1 or a base sequence complementary thereto. Also disclosed is a method for controlling chromogenesis in test materials and for screening for expression control materials of chromogenic genes. The composition and the screening methodcan be used for the whitening effect or for the prevention of gray hair.

11 Claims, 4 Drawing Sheets

SEQUENCE LISTING

<160> NUMBER OF SEQ ID NOS: 2

<210> SEQ ID NO 1
<211> LENGTH: 22
<212> TYPE: RNA
<213> ORGANISM: Artificial Sequence
<220> FEATURE:
<223> OTHER INFORMATION: synthetic construct (hsa-mir-125b)

<400> SEQUENCE: 1
ucccugagac ccuaacuugu ga     22

<210> SEQ ID NO 2
<211> LENGTH: 22
<212> TYPE: RNA
<213> ORGANISM: Artificial Sequence
<220> FEATURE:
<223> OTHER INFORMATION: synthetic construct (antisense hsa-mir-125b)

<400> SEQUENCE: 2
ucacaaguua gggucucagg ga     22

COMPOSITION FOR CONTROLLING CHROMOGENESIS INCLUDING MICRORNA

CROSS REFERENCE TO RELATED APPLICATIONS

This application is a National Stage of International Application No. PCT/KR2012/004645, filed Jun. 13, 2012, claiming priority based on Korean Patent Application No. 10-2011-0061107, filed Jun. 23, 2011, the contents of all of which are incorporated herein by reference in their entirety.

TECHNICAL FIELD

The present invention relates to the identification of hsa-miR-125b (hereinafter referred to as miR-125b) that is microRNA (hereinafter referred to as miRNA) that regulates pigmentation and the expression of a pigmentation gene, and more particularly to a whitening cosmetic composition or a pharmaceutical composition comprising miR-125b or its mimic and to a cosmetic composition or a pharmaceutical composition for preventing gray hair, which comprises an inhibitor of miR-125b.

BACKGROUND ART miRNA is a kind of 20-25-nucleotide endogenous small RNA present in cells. It is derived from a DNA that produces no protein, and is generated from hairpin-shaped transcripts. miRNA functions as a repressor that binds to the complementary sequence of 3'-UTR of its target mRNA to induce the inhibition of translation or unstabilization of the target mRNA, and ultimately repress the protein synthesis of the target mRNA. It is known that one miRNA targets several mRNAs and mRNA may also be controlled by several miRNAs.

miRNA is currently known to play a very important role in a number of biological processes including regulation of developmental timing, apoptosis, fat metabolism, and hematopoietic cell differentiation among others, and thus has received a great deal of attention in the field of life science. However, while studies on the function of miRNA in the processes of development of diseases such as cancer have considerably progressed, studies on the role of miRNA in the skin science are relatively insufficient. Recently, it was reported that miR-203 targets p63 mRNA in keratinocytes to inhibit the differentiation of the keratinocytes and that miR-125b inhibits the differentiation of skin stem cells and inhibits the division of keratinocytes, but there are little or no reports of skin-related specific miRNA and the function thereof. In addition to miR-203 and miR-125b, several specific miRNAs are sufficiently expected to play a biologically important role in the skin. In addition, miRNA can be used in various applications, including biological markers and materials, and thus it is concluded that studies on the function of miRNA in the skin can be applied in various fields, including the cosmetic and medical fields.

The skin is roughly divided into epidermis and dermis, and melanocytes present in epidermis synthesize a pigment (melanin) that shows the inherent color of the skin. Biological factors that control skin pigments can be roughly divided into factors that make melanosome in melanocytes, and factors that transport melanosome. Of the factors that make melanosome, the most well-known factors include tyrosinase (TYR) and the like, and factors known to be involved in melanosome transport include Rab27a and the like. Recently, it was known that transcription factors such as PAX3, MITF and the like also participate in the pigment regulation process. Thus, these factors that regulate the pigment become important targets for skin whitening, black hair production or gray hair prevention.

DISCLOSURE

Technical Problem

The present inventors have conducted studies to find miRNA that is involved in the pigmentation of WM266-4 melanoma cells in which skin pigmentation genes are highly expressed. As a result, the present inventors have found that hsa-miR-125b inhibits the expression of tyrosinase mRNA and regulates pigmentation.

It is, therefore, an object of the present invention to provide a composition for skin whitening, comprising miR-125b or its mimic.

Another object of the present invention is to provide a composition for preventing gray hair, comprising an inhibitor of miR-125b.

Technical Solution

In order to accomplish the above objects, the present invention provides a composition for regulating pigmentation and pigmentation gene expression, the composition comprising an miRNA of SEQ ID NO: 1 as an active ingredient.

The present invention also provides a composition for regulating pigmentation and pigmentation gene expression, the composition comprising, as an active ingredient, an antisense nucleic acid molecule of SEQ ID NO: 2, which has a nucleotide sequence complementary to SEQ ID NO: 1 of SEQ ID NO: 1 and is capable of hybridizing to the miRNA.

The present invention also provides a method for screening a substance that regulates pigmentation and pigmentation gene expression, the method comprising the steps of: (a) transfecting a cell with an miRNA of SEQ ID NO: 1 or an antisense nucleic acid molecule of SEQ ID NO: 2; (b) treating the cell with a test substance; (c) determining whether the test substance inhibits the pigmentation gene expression or whether it stimulates the pigmentation gene expression; and (d) determining whether color of the cell changes.

Advantageous Effects

The inventive composition comprising the miRNA of SEQ ID NO: 1 or the antisense nucleic acid molecule of SEQ ID NO: 2 can exhibit a skin whitening effect or a gray hair-preventing effect by regulating the expression of tyrosinase mRNA that is a pigmentation gene and regulating pigmentation.

BEST MODE

Hereinafter, the present invention will be described in detail.

The present invention provides an miRNA of SEQ ID NO: 1, which regulates pigmentation and the expression of a pigmentation gene.

In the present invention, the pigmentation gene is tyrosinase mRNA.

5'-ucccugagacccuaacuuguga-3' (SEQ ID NO: 1)

The miRNA that is used in the present invention is an oligonucleotide having the nucleotide sequence of SEQ ID NO: 1 and consisting of 22 consecutive nucleotides including cccugag. In addition, the miRNA includes those that comprise the nucleotide sequence of SEQ ID NO: 1 and function to regulate pigmentation and the expression of pigmentation genes.

The miRNA can inhibit pigmentation and the expression of genes that are involved in pigmentation.

In an embodiment of the present invention, an oligonucleotide, which is a mimic of hsa-miR-125b and has the same sequence as that of hsa-miR-125b, can be prepared using the miRNA of SEQ ID NO: 1. In addition, the mimic of hsa-miR-125b includes those that comprise the nucleotide sequence of hsa-miR-125b and function to regulate pigmentation and the expression of pigmentation genes.

An embodiment of the present invention provides an antisense nucleic acid molecule of SEQ ID NO: 2, which has a nucleotide sequence complementary to the miRNA of SEQ ID NO: 1 and is capable of hybridizing to the miRNA. The antisense nucleic acid molecule of SEQ ID NO: 2 is an inhibitor of miR-125b and can hybridize to the miRNA. In addition, the inhibitor of miR-125b includes those that comprise the nucleotide sequence of SEQ ID NO: 2 and can hybridize to the miRNA.

```
                                            (SEQ ID NO: 2)
        5'-ucacaaguuagggucucaggga -3'
```

The present invention provides a composition for regulating pigmentation and pigmentation gene expression, the composition comprising, as an active ingredient, the miRNA of SEQ ID NO: 1 or the antisense nucleic acid molecule of SEQ ID NO: 2.

The composition of the present invention is a composition for inhibiting or stimulating the expression of a pigmentation gene, and the pigmentation gene is tyrosinase mRNA.

The composition of the present invention functions to inhibit or stimulate pigmentation and comprises, as an active ingredient, the miRNA that is selected from oligonucleotides having the nucleotide sequence of SEQ ID NO: 1 and consisting of 22 consecutive nucleotides including cccugag. In addition, examples of the miRNA include those that comprise the nucleotide sequence of SEQ ID NO: 1 and function to regulate pigmentation and the expression of pigmentation genes.

The composition of the present invention comprises, as an active ingredient, the antisense nucleic acid molecule that is selected from among oligonucleotides having the nucleotide sequence of SEQ ID NO: 2 and consists of 22 consecutive nucleotides. The antisense nucleic acid molecule is an inhibitor of miR-125b and can hybridize to the miRNA. In addition, the inhibitor of miR-125b includes those that comprise the nucleotide sequence of SEQ ID NO: 2 and can hybridize to the miRNA.

In the present invention, the miRNA of SEQ ID NO: 1, the antisense nucleic acid molecule of SEQ ID NO: 2, or the oligonucleotide comprising the nucleotide sequence of SEQ ID NO: 1 or 2, may be used in an amount of 0.00001-30.0 wt % based on the total weight of the composition.

Specifically, the composition comprising, as an active ingredient, the miRNA of SEQ ID NO: 1 or an oligonucleotide comprising the nucleotide sequence of SEQ ID NO: 1, can provide a skin whitening effect by inhibiting the expression of pigmentation genes, particularly to tyrosinase mRNA.

In addition, the composition comprising, as an active ingredient, the antisense nucleic acid molecule of SEQ ID NO: 2 or an oligonucleotide comprising the nucleotide sequence of SEQ ID NO: 2, can provide a gray hair-preventing effect by stimulating the expression of pigmentation genes, particularly to tyrosinase mRNA.

The composition of the present invention may preferably be formulated as a cosmetic composition or a pharmaceutical composition, but is not specifically limited thereto.

When the composition of the present invention is a cosmetic formulation, it contains a cosmetically acceptable medium or base. It may be provided in any form suitable for topical application. For example, it may be provided in the form of solution, gel, solid, kneaded anhydrous product, oil-in-water emulsion, suspension, micro-emulsion, microcapsule, microgranule, or ionic (liposome) and/or non-ionic vesicle dispersion. In addition, it may be provided in the form of cream, skin toner, lotion, powder, ointment, spray, or concealed stick. The composition of the present invention may be prepared according to a conventional method known in the art.

When the composition of the present invention is a pharmaceutical composition, it may be formulated as a solid, semi-solid or liquid parenteral dosage form (for injection, transdermal application or external application) by a conventional inorganic or organic carrier to the miRNA of SEQ ID NO: 1, the antisense nucleic acid molecule of SEQ ID NO: 2 or an oligonucleotide comprising the nucleotide sequence of SEQ ID NO: 1 or 2, which is an active ingredient. Formulations for parenteral administration include a formulation for topical administration, an ointment, lotion, a spray formulation, a suspension and the like.

The active ingredient of the composition according to an embodiment of the present invention can be easily formulated according to a conventional method by suitable use of a surfactant, an excipient, a colorant, a flavoring agent, a preservative, a stabilizer, a buffer, a suspending agent, or other conventional additives.

The dose of the miRNA according to an embodiment of the present invention may vary depending on the age, sex and weight of the subject to be treated, a particular disease or pathological condition to be treated, the severity of the disease or pathological condition, the route of administration, and the physician's judgment. The dose based on such factors can be easily determined by those skilled in the art. Formulations other than an injectable formulation may be applied to a pigmented area using a method known to those skilled in the art, and injectable formulation may be topically injected into a pigmented area.

The miRNA of the present invention may also be composed of a modified oligonucleotide. For example, it may partially or fully comprise an oligonucleotide comprising 2'-O-alkyl (e.g., methyl or ethyl), 2'-O-allyl, or 2'-substituted ribose such as 2'-O-allyl. In addition, it may partially or fully comprise an oligonucleotide having a substituted base.

An embodiment of the present invention provides a method for screening a substance that regulates pigmentation and pigmentation gene expression, the method comprising the steps of: (a) transfecting a cell with an miRNA of SEQ ID NO: 1 or an antisense nucleic acid molecule of SEQ ID NO: 2; (b) treating the cell with a test substance; (c) determining whether the test substance inhibits the pigmentation gene expression or whether it stimulates the pigmentation gene expression; and (d) determining whether color of the cell changes.

In the step of transfecting the cell with the miRNA of SEQ ID NO: 1 or the antisense nucleic acid molecule of SEQ ID NO: 2, the transfecting may be performed using microinjection, calcium phosphate co-precipitation, electroporation, or a liposome-based method, but is not limited thereto.

In the method for screening the agent that regulates melanin production according to an embodiment of the present invention, whether the test substance regulates the pigmentation gene expression may be determined using RT-PCR, ELISA or Western immunoblot analysis, which is well known in the art.

Screening the expression regulating substance based on the expression level of pigmentation genes according to an embodiment of the present invention may be performed by an immunoassay (e.g., ELISA or immunoblot assay) to determine whether the test substance inhibits the expression of the pigmentation genes or whether it stimulates the expression.

In an embodiment of the present invention, the method for screening a substance that regulates pigmentation and pigmentation gene expression may further comprise determining the test material to be an agent that stimulates the pigmentation gene expression, when the test substance is determined to increase the pigmentation of the cell or increase the expression, activity or function of the pigmentation gene, and determining the test substance to be an agent that inhibits the pigmentation gene expression, when the test material is determined to reduce the pigmentation of the cell or reduce the expression, activity or function of the pigmentation gene.

MODE FOR INVENTION

Hereinafter, the present invention will be described in further detail with reference to examples and test examples. It is to be understood, however, that these examples and test examples are for illustrative purposes and are not intended to limit the scope of the present invention.

TEST EXAMPLE 1

Reduction in Tyrosinase mRNA by Mimic of hsa-miR-125b

The present inventors used a mimic of hsa-miR-125b to perform a gain-of-function study of hsa-miR-125b, in which the mimic of hsa-miR-125b is an oligonucleotide having the same sequence as that of hsa-miR-125b and can be transfected into cells to induce the overexpression of hsa-miR-125b in the cells.

20 uM of a mimic of hsa-miR-125b (Model: C-300595-03-0005, miRIDIAN Mimic, Human hsa-miR-125b MIMAT0000423/MI0000446 (hsa-miR-125b), 5 nmol, Dharmacon, Inc.; Example 1) was transfected into the melanoma cell line WM266-4 using liposome and allowed to move into the cells. In control groups, a sample (Comparative Example 1) containing no oligonucleotide and a sample (Comparative Example 2) transfected with an oligonucleotide (model: CN-001000-01-05, miRIDIAN microRNA Mimic Negative Control #1, Dharmacon, Inc.) that does not overlap with the miRNA of the present invention were used. After transfection, the cells were cultured in a 5% $CO_2$ incubator at 37° C. for about 60 hours, and then RNA was isolated from the cells using 1 ml of Trizol reagent. Specifically, the cells were lysed using Trizol, and then centrifuged to remove the supernatant, and 0.35 ml of isopropanol was added to the residue to form nucleic acid pellets, which were then washed with 70% EtOH and dissolved in water to isolate RNA. About 1 ug of the RNA was made into cDNA using oligo dT and reverse transcriptase, and the cDNA was subjected to real-time PCR according to the TaqMan method (Applied Biosystems) using a primer (assay ID: Hs01099965_m1) specific to tyrosinase mRNA under the following conditions: reaction at 95° C. for 10 min; and then about 45 cycles of 10 sec at 95° C. and 1 min at 60° C. The expression level of tyrosinase mRNA was normalized to the mRNA expression of the housekeeping gene GAPDH (assay ID: 4333764F), and the results of the normalization are shown in FIG. 1.

Figure 1:
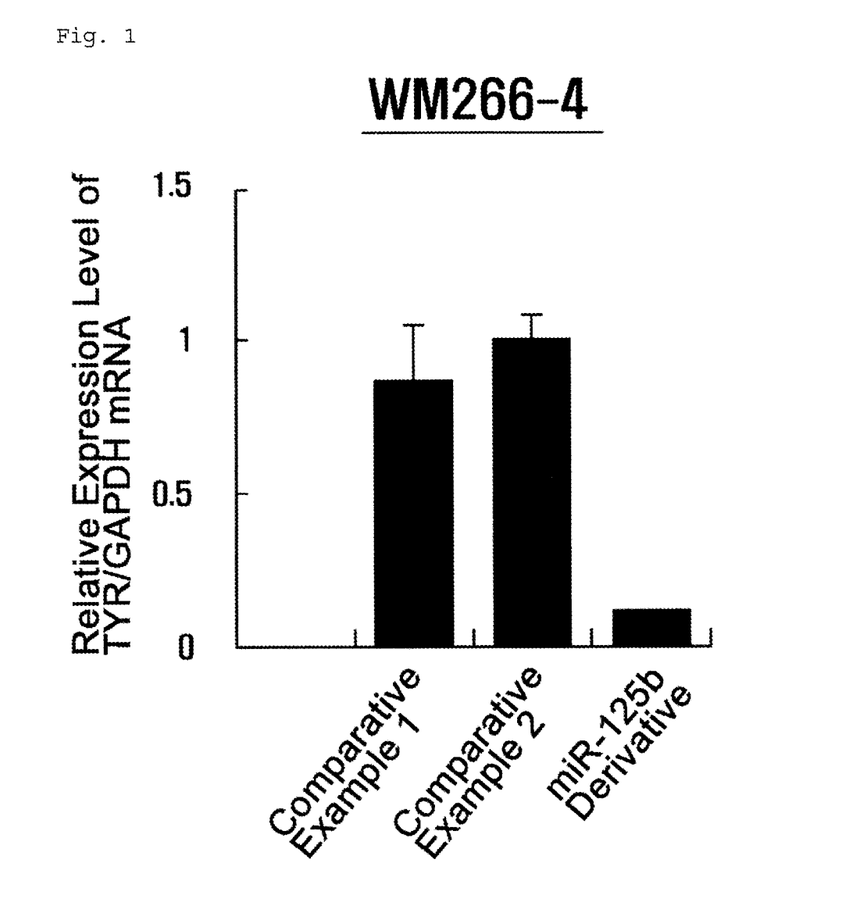
FIG. 1 shows the results obtained by transfecting a cell with an oligonucleotide having the same sequence as that of hsa-miR-125b to induce the overexpression of hsa-miR-125b and performing real-time PCR to determine the expression level of tyrosinase mRNA in the cell (TYR: tyrosinase).

As a result, it could be seen that the expression level of tyrosinase mRNA in the cells transfected with the hsa-miR-125b mimic (Example 1) significantly decreased compared to those in Comparative Examples 1 and 2 (FIG. 1).

TEST EXAMPLE 2

Reduction in Tyrosinase Protein by Mimic of hsa-miR-125b

The present inventors used a mimic of hsa-miR-125b to perform a gain-of-function study of hsa-miR-125b, in which the mimic of hsa-miR-125b is an oligonucleotide having the same sequence as that of hsa-miR-125b and can be transfected into cells to induce the overexpression of hsa-miR-125b in the cells.

20 uM of a mimic of hsa-miR-125b (Model: C-300595-03-0005, miRIDIAN Mimic, Human hsa-miR-125b MIMAT0000423/MI0000446 (hsa-miR-125b), 5 nmol, Dharmacon, Inc.; Example 1) was transfected into the melanoma cell line WM266-4 using liposome and allowed to move into the cells. In control groups, a sample (Comparative Example 1) containing no oligonucleotide and a sample (Comparative Example 2) transfected with an oligonucleotide (model: CN-001000-01-05, miRIDIAN microRNA Mimic Negative Control #1, Dharmacon, Inc.) that does not overlap with the miRNA of the present invention were used. At about 60 hours after the transfection, the cell membrane was lysed using RIPA buffer, and the cells were centrifuged to extract the protein-containing supernatant. Then, about 10 ug of the protein was quantified using the BCA method. The quantified protein was subjected to Western blot analysis, in which the amount of the tyrosinase protein was observed using an antibody (05-647, Upstate Inc.) specific to the tyrosinase. The expression level of the tyrosinase protein was normalized to the protein expression level of the housekeeping gene GAPDH, and the results of the normalization are shown in FIG. 2.

Figure 2:
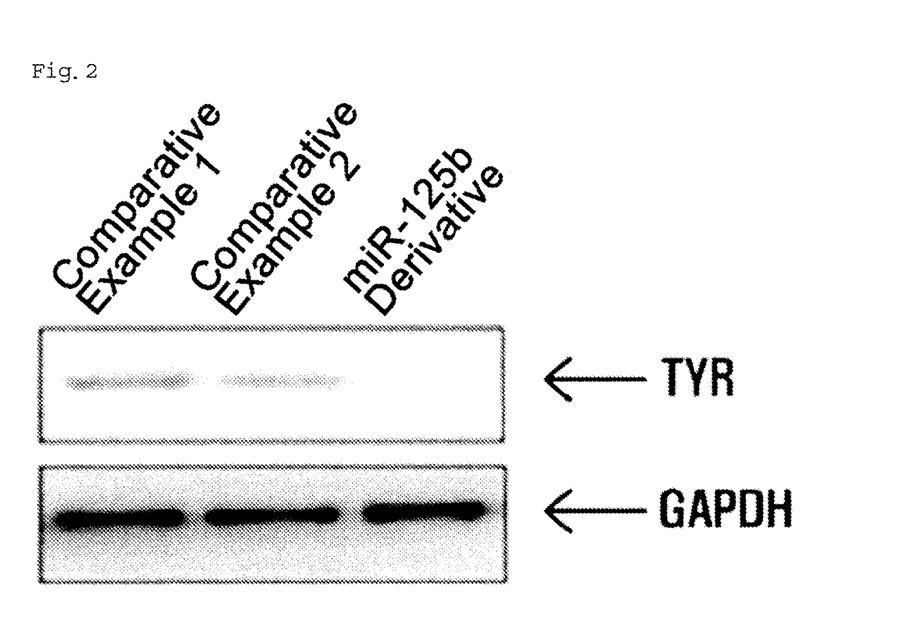
FIG. 2 shows the results obtained by transfecting a cell with an oligonucleotide having the same sequence as that of hsa-miR-125b to induce the overexpression of hsa-miR-125b and performing Western immunoblot analysis to determine the expression level of tyrosinase protein in the cell (TYR: tyrosinase).

As a result, it could be seen that the expression level of tyrosinase mRNA in the cells transfected with the hsa-miR-125b mimic (Example 1) significantly decreased compared to those in Comparative Examples 1 and 2 (FIG. 2).

TEST EXAMPLE 3

Increase in Tyrosinase mRNA by Inhibitor of hsa-miR-125b

The present inventors used an inhibitor of miR-124b to perform a loss-of-function study of miR-125b, in which the inhibitor of miR-125b is an oligonucleotide having a sequence complementary to that of miR-125b and can bind to miR-125b in cells to inhibit the function of the miR-125b.

75 uM of an inhibitor of miR-125b (model: IH-300595-05-0005, miRIDIAN Hairpin Inhibitor, Human hsa-miR-125b MIMAT0000423/MI0000446 (hsa-miR-125b), Dharmacon, Inc.; Example 2) was transfected into the melanoma cell line WM115 using liposome and allowed to move into the cells. In control groups, a sample (Comparative Example 1) containing no oligonucleotide and a sample (Comparative Example 2) transfected with an oligonucleotide (model: CN-001000-01-05, miRIDIAN microRNA Mimic Negative Control #1, Dharmacon, Inc.) that does not overlap with the miRNA of the present invention were used. After transfection, the cells were cultured in a 5% $CO_2$ incubator at 37° C. for about 60 hours, and then RNA was isolated from the cells using 1 ml of Trizol reagent. Specifically, the cells were lysed using Trizol, and then centrifuged to remove the supernatant, and 0.35 ml of isopropanol was added to the residue to form nucleic acid pellets, which were then washed with 70% EtOH and dissolved in water to isolate RNA. About 1 ug of the RNA was made into cDNA using oligo dT and reverse transcriptase, and the cDNA was subjected to real-time PCR according to the TaqMan method (Applied Biosystems) using a primer (assay ID: Hs01099965_m1) specific to tyrosinase mRNA under the following conditions: reaction at 95° C. for 10 min; and then about 45 cycles of 10 sec at 95° C. and 1 min at 60° C. The expression level of tyrosinase mRNA was normalized to the mRNA expression of the housekeeping gene GAPDH (assay ID: 4333764F), and the results of the normalization are shown in FIG. 3.

Figure 3:
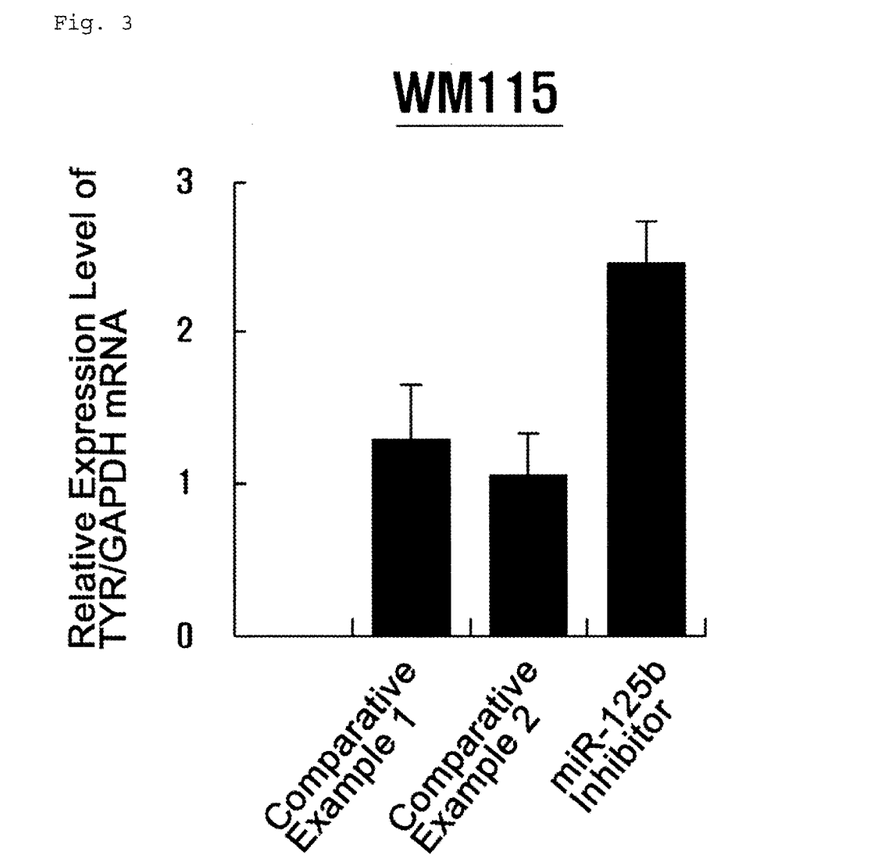
FIG. 3 shows the results obtained by transfecting a cell with an oligonucleotide having a sequence complementary to that of hsa-miR-125b to allow the oligonucleotide to bind to miR-125b present in the cell so as to inhibit the function of the miR-125b and performing real-time PCR to determine the expression level of tyrosinase mRNA in the cell (TYR: tyrosinase).

As a result, it could be seen that the expression level of tyrosinase mRNA in the cells transfected with the inhibitor of hsa-miR-125b (Example 2) significantly increased compared to those in Comparative Examples 1 and 2 (FIG. 3).

TEST EXAMPLE 4

Reduction in Expression Level of hsa-miR-125b by Treatment with Forskolin

The present inventors treated cells with forskolin known to increase the expression level of pigmentation genes, thereby inducing the condition of increasing the expression level of pigmentation genes by forskolin, and then examined whether the expression level of hsa-miR-125b in the cells changed.

Specifically, the melanoma cell line WM266-4 was incubated in FES-free medium overnight, and then treated with 25 uM and 50 uM of forskolin. After about 6 hours, RNA was isolated from the cells using 1 ml of Trizol reagent. Specifically, the cells were lysed using Trizol, and then centrifuged to remove the supernatant, and 0.35 ml of isopropanol was added to the residue to form nucleic acid pellets, which were then washed with 70% EtOH and dissolved in water to isolate RNA. Then, real-time PCR was performed using a hsa-miR-125b-specific primer (assay ID: 000449) according to the TaqMan method (Applied Biosystems). The RNA was made into cDNA specific to hsa-miR-125b using a stem-loop primer specific to hsa-miR-125b and reverse transcriptase, and the expression level of hsa-miR-125b mRNA was observed using a primer specific to hsa-miR-125b. The expression level of hsa-miR-125b mRNA was normalized to the small RNA expression level of the housekeeping gene rnu6b, and the results of the normalization are shown in FIG. 4.

Figure 4:
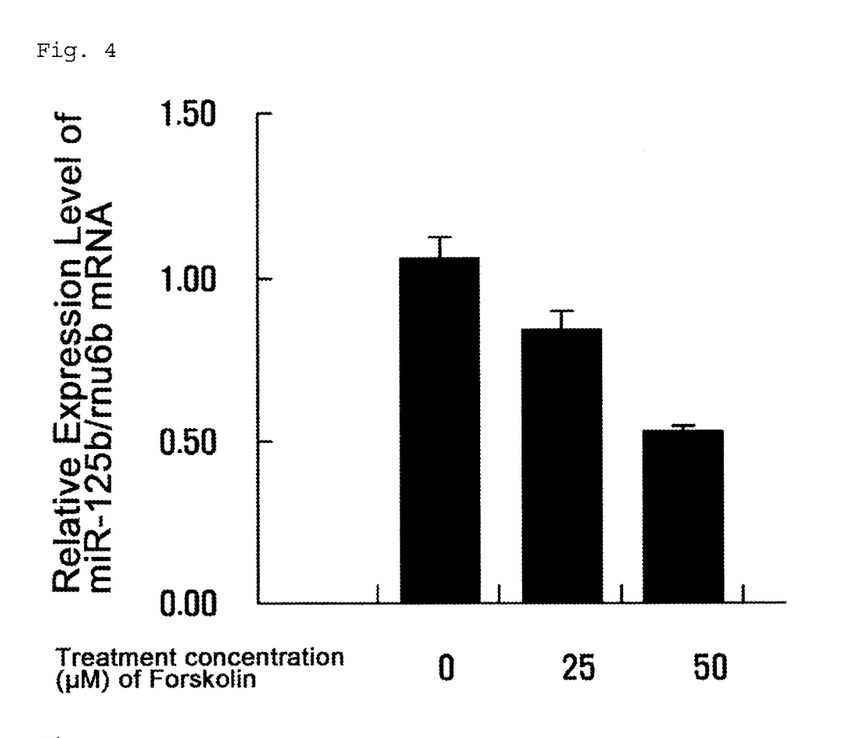
FIG. 4 shows the results obtained by treating the WM266-4 cell line with forskolin known to increase the expression of pigmentation-related genes, thereby inducing an increase in the expression of the pigmentation-related genes, real-time PCR capable of determining the expression level of miR-125b, thereby determining the expression level of miR-125b as a function of the treatment concentration of forskolin.

As a result, it could be seen that the expression level of has-miR-125b in the cells treated with forskolin decreased as the treatment concentration of forskolin increased (FIG. 4).

TEST EXAMPLE 5

Reduction in Pigmentation by Mimic of hsa-miR-125b

The present inventors used to a mimic of hsa-miR-125b to perform a gain-of-function study of hsa-miR-125b, in which the mimic of hsa-miR-125b is an oligonucleotide having the same sequence as that of hsa-miR-125b and can be transfected into cells to induce the overexpression of hsa-miR-125b in the cells.

Figure 5:
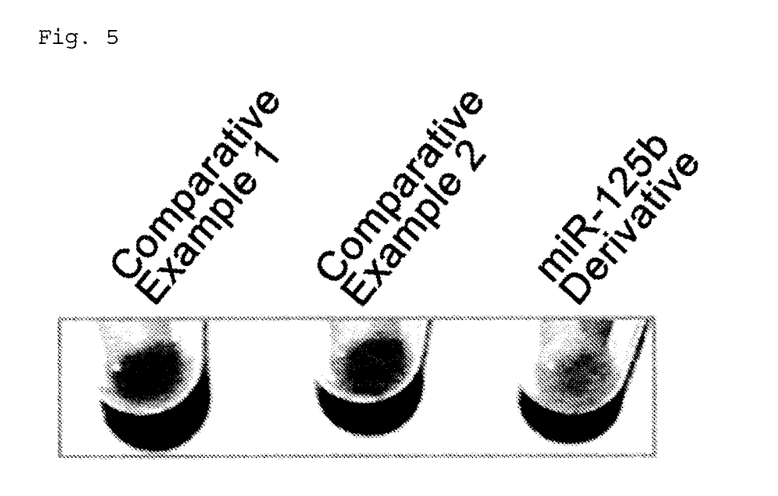
FIG. 5 shows the results obtained by transfecting human primary melanocytes with an oligonucleotide having the same sequence as that of hsa-miR-125b to induce the overexpression of hsa-miR-125b in the cells, centrifuging the cells to obtain cell pellets, and observing the color of the cell pellets to determine a change in the pigmentation of the cells.

20 uM of a mimic of hsa-miR-125b (model: C-300595-03-0005, miRIDIAN Mimic, Human hsa-miR-125b MIMAT0000423/MI0000446 (hsa-miR-125b), 5 nmol, Dharmacon, Inc.; Example 1) was transfected into human primary melanocytes using liposome and allowed to move into the cells. In control groups, a sample (Comparative Example 1) containing no oligonucleotide and a sample (Comparative Example 2) transfected with an oligonucleotide (model: CN-001000-01-05, miRIDIAN microRNA Mimic Negative Control #1, Dharmacon, Inc.) that does not overlap with the miRNA of the present invention were used. At 7 days after the transfection, the cells were washed twice with 5 ml of PBS buffer, and 1 ml of PBS buffer was added thereto. Then, the cells were scrapped using a scrapper and centrifuged at 13000 rpm for 5 minutes to make cell pellets, and the color of the cell pellets was observed to determine the degree of pigmentation. The results of the observation are shown in FIG. 5.

As a result, Comparative Examples 1 and 2 showed a deep brown color due to pigmentation. However, the cells transfected with the hsa-miR-125b mimic (Example 1) showed a light yellow color, suggesting that the pigmentation of the cells was significantly inhibited (FIG. 5).

The above results suggest that hsa-miR-125b and its mimic regulate pigmentation.

The inventive skin whitening composition containing the miRNA of SEQ ID NO: 1 as an active ingredient can be prepared as described in the following Formulation Examples, but is not limited thereto.

FORMULATION EXAMPLE 1

Moisture Lotion

According to the composition shown in Table 1 below, a moisture lotion can be prepared using a conventional method.

TABLE 1

| Components | Contents (wt %) |
|---|---|
| Glycerin | 8.0 |
| Butylene glycol | 4.0 |
| Hyaluronic acid extract | 5.0 |
| Beta-glucan | 7.0 |
| Carbomer | 0.1 |
| miRNA of SEQ ID NO: 1 | 0.1 |
| Caprylic/capric triglyceride | 8.0 |
| Squalane | 5.0 |
| Cetearyl glucoside | 1.5 |
| Sorbitan stearate | 0.4 |
| Cetearyl alcohol | 1.0 |
| Preservative | q.s. |
| Fragrance | q.s. |
| Pigment | q.s. |
| Triethanolamine | 0.1 |
| Purified water | Balance |

FORMULATION EXAMPLE 2

Milk Lotion

According to the composition shown in Table 2 below, a milk lotion can be prepared using a conventional method.

TABLE 2

| Components | Contents (wt %) |
|---|---|
| Purified water | Balance |
| Glycerin | 3.0 |
| Butylene glycol | 3.0 |
| Liquid paraffin | 5.0 |
| Beta-glucan | 7.0 |
| Carbomer | 0.1 |
| miRNA of SEQ ID NO: 1 | 3.0 |
| Caprylic/capric triglyceride | 3.0 |
| Squalane | 5.0 |
| Cetearyl glucoside | 1.5 |
| Sorbitan stearate | 0.4 |
| Polysorbate 60 | 1.5 |
| Preservative | q.s. |
| Fragrance | q.s. |
| Pigment | q.s. |
| Triethanolamine | 0.1 |

FORMULATION EXAMPLE 3

Nourishing Cream

According to the composition shown in Table 3 below, a nourishing cream can be prepared using a conventional method.

TABLE 3

| Components | Contents (wt %) |
|---|---|
| Glycerin | 3.0 |
| Butylene glycol | 3.0 |
| Liquid paraffin | 7.0 |
| Beta-glucan | 7.0 |
| Carbomer | 0.1 |
| miRNA of SEQ ID NO: 1 | 3.0 |
| Caprylic/capric triglyceride | 3.0 |
| Squalane | 5.0 |
| Cetearyl glucoside | 1.5 |
| Sorbitan stearate | 0.4 |
| Polysorbate 60 | 1.2 |
| Preservative | q.s. |
| Fragrance | q.s. |

TABLE 3-continued

| Components | Contents (wt %) |
|---|---|
| Pigment | q.s. |
| Triethanolamine | 0.1 |
| Purified water | Balance |

FORMULATION EXAMPLE 4

Massage Cream

According to the composition shown in Table 4 below, a massage cream can be prepared using a conventional method.

TABLE 4

| Components | Contents (wt %) |
|---|---|
| Glycerin | 8.0 |
| Butylene glycol | 4.0 |
| Liquid paraffin | 45.0 |
| Beta-glucan | 7.0 |
| Carbomer | 0.1 |
| miPNA of SEQ ID NO: 1 | 1.0 |
| Caprylic/capric triglyceride | 3.0 |
| Beeswax | 4.0 |
| Cetearyl glucoside | 1.5 |
| Sorbitan sesquioleate | 0.9 |
| Vaseline | 3.0 |
| Preservative | q.s. |
| Fragrance | q.s. |
| Pigment | q.s. |
| Paraffin | 1.5 |
| Purified water | Balance |

FORMULATION EXAMPLE 5

Pack

According to the composition shown in Table 5 below, a pack formulation can be prepared using a conventional method.

TABLE 5

| Components | Contents (wt %) |
|---|---|
| Glycerin | 4.0 |
| Polyvinyl alcohol | 15.0 |
| Hyaluronic acid extract | 5.0 |
| Beta-glucan | 7.0 |
| Allantoin | 0.1 |
| miRNA of SEQ ID NO: 1 | 0.5 |
| Nonyl phenylether | 0.4 |
| Polysorbate 60 | 1.2 |
| Preservative | q.s. |
| Fragrance | q.s. |
| Pigment | q.s. |
| Ethanol | 6.0 |
| Purified water | Balance |

FORMULATION EXAMPLE 6

Ointment

According to the composition shown in Table 6 below, an ointment can be prepared using a conventional method.

TABLE 6

| Components | Contents (wt %) |
|---|---|
| Glycerin | 8.0 |
| Butylene glycol | 4.0 |
| Liquid paraffin | 15.0 |
| Beta-glucan | 7.0 |
| Carbomer | 0.1 |
| miRNA of SEQ ID NO: 1 | 1.0 |
| Caprylic/capric triglyceride | 3.0 |
| Squalane | 1.0 |
| Cetearyl glucoside | 1.5 |
| Sorbitan stearate | 0.4 |
| Cetearyl alcohol | 1.0 |
| Preservative | q.s. |
| Fragrance | q.s. |
| Pigment | q.s. |
| Beeswax | 4.0 |
| Purified water | Balance |

The inventive composition for preventing gray hair, which contains the miRNA of SEQ ID NO: 2, can be prepared as described in the following Formulation Examples, but is not limited thereto.

FORMULATION EXAMPLE 7

Hair Shampoo

According to the composition shown in Table 7 below, a hair shampoo can be prepared using a conventional method.

TABLE 7

| Components | Contents (wt %) |
|---|---|
| Sodium lauryl sulfate solution (30%) | 20.0 |
| Palm oil fatty acid diethanolamide | 5.0 |
| Polyquaternium-10 | 0.3 |
| Propylene glycol | 2.0 |
| miRNA of SEQ ID NO: 2 | 0.1 |
| Piroctone olamine | 0.5 |
| Yellow No. 203 | q.s. |
| p-oxybenzoic acid ester | 0.2 |
| Combined fragrance | q.s. |
| Citric acid | q.s. |
| Purified water | Balance |

FORMULATION EXAMPLE 8

Hair Conditioner

According to the composition shown in Table 8 below, a hair conditioner can be prepared using a conventional method.

TABLE 8

| Components | Contents (wt %) |
|---|---|
| Cetyltrimethylammonium chloride (29%) | 7.0 |
| Distearyldimethylammonium chloride (75%) | 4.0 |
| Cetostearyl alcohol | 3.5 |
| Polyoxyethylene stearylether | 1.0 |
| Liquid paraffin | 2.0 |
| Propylene glycol | 1.5 |
| miRNA of SEQ ID NO: 2 | 0.1 |
| Combined fragrance | q.s. |
| Citric acid | q.s. |
| Purified water | Balance |

FORMULATION EXAMPLE 9

Scalp Hair Tonic

According to the composition shown in Table 9 below, a scalp hair tonic can be prepared using a conventional method.

TABLE 9

| Components | Contents (wt %) |
|---|---|
| Menthol | 0.1 |
| D-panthenol | 0.6 |
| Salicylic acid | 0.05 |
| Glycerin | 1.0 |
| Polyoxyethylene hydrogenated castor oil | 0.8 |
| Tocopherol acetate | 0.03 |
| Combined fragrance | q.s. |
| miRNA of SEQ ID NO: 2 | 0.1 |
| Ethanol | 30.0 |
| Purified water | Balance |

FORMULATION EXAMPLE 10

Scalp Essence

According to the composition shown in Table 10 below, a scalp essence can be prepared using a conventional method.

TABLE 10

| Components | Contents (wt %) |
|---|---|
| Ethanol | 30.0 |
| Polysorbate 60 | 1.5 |
| Glycerin | 3.0 |
| Carboxyvinyl polymer | 0.1 |
| Triethanolamine | 0.2 |
| miRNA of SEQ ID NO: 2 | 0.1 |
| Preservative | q.s. |
| Fragrance and pigment | q.s. |
| Purified water | Balance |

FORMULATION EXAMPLE 11

Injectable Formulation

According to the composition shown in Table 11 below, an injectable formulation can be prepared using a conventional method.

TABLE 11

| Components | Weight (per ml) |
|---|---|
| Sodium chloride | 9 mg |
| Sodium carboxymethylcellulose | 30.0 mg |
| Tween 20 | 1.0 mg |
| miRNA of SEQ ID NO: 2 | 1 mg |
| Distilled water for injection | Balance |

FORMULATION EXAMPLE 12

Ointment

According to the composition shown in Table 12 below, an ointment can be prepared using a conventional method.

TABLE 12

| Components | Contents (wt %) |
|---|---|
| Caprylic/capric triglyceride | 10 |
| Liquid paraffin | 10 |
| Sorbitan sesquioleate | 6 |
| Octyldodeceth-25 | 9 |
| Cetyl ethylhexanoate | 10 |
| Squalane | 1 |
| Salicylic acid | 1 |
| Glycerin | 15 |
| Sorbitol | 1 |
| miRNA of SEQ ID NO: 2 | 0.1 |
| Preservative, pigment and fragrance | q.s. |
| Purified water | Balance |

FORMULATION EXAMPLE 13

Lotion

According to the composition shown in Table 13 below, a lotion can be prepared using a conventional method.

TABLE 13

| Components | Contents (wt %) |
|---|---|
| miRNA of SEQ ID NO: 2 | 0.1 |
| Beeswax | 4.0 |
| Polysorbate 60 | 1.5 |
| Sorbitan sesquioleate | 1.5 |
| Liquid paraffin | 0.5 |
| Caprylic/capric triglyceride | 5.0 |
| Glycerin | 3.0 |
| Butylene glycol | 3.0 |
| Propylene glycol | 3.0 |
| Carboxyvinyl polymer | 0.1 |
| Triethanolamine | 0.2 |
| Preservative, pigment and fragrance | q.s. |
| Purified water | Balance |

FORMULATION EXAMPLE 14

Spray formulation

According to the composition shown in Table 14 below, a spray formulation can be prepared using a conventional method.

TABLE 14

| Components | Contents (wt %) |
|---|---|
| miRNA of SEQ ID NO: 2 | 0.1 |
| Ethanol | 80 |
| Tween 80 | 5 |
| Glycerol | 5 |
| Tocopherol acetate | 1 |
| Preservative, pigment and fragrance | q.s. |
| Purified water | Balance |

SEQUENCE LIST TEXT

SEQ ID NO: 1 is the nucleotide sequence of an miRNA that is used in the present invention and regulates the expression of pigmentation genes, and it consists of 22 consecutive nucleotides including cccugag.

SEQ ID NO: 2 is an inhibitor of miR-125b that is used in the present invention, and it can hybridize to miR-125b that is used in the present invention.

---

The invention claimed is:

1. A method for screening a substance that regulates an expression of tyrosinase gene, the method comprising the steps of:
   (a) transfecting a cell with a miRNA of SEQ ID NO: 1 or an antisense nucleic acid molecule of SEQ ID NO: 2;
   (b) treating the cell with a test substance;
   (c) determining whether the test substance inhibits the tyrosinase gene expression or whether it stimulates the tyrosinase gene expression; and
   (d) determining whether color of the cell changes.

2. The method of claim 1, further comprising, after step (c), a step of determining the test substance to be an agent that stimulates the tyrosinase gene expression, when the test substance is determined to increase the expression, activity or function of the tyrosinase gene.

3. The method of claim 1, further comprising, after step (c), a step of determining the test substance to be an agent that inhibits the tyrosinase gene expression, when the test substance is determined to reduce the expression, activity or function of the tyrosinase gene.

4. The method of claim 1, further comprising, after step (d), a step of determining the test substance to be an agent that stimulates the tyrosinase gene expression, when the pigmentation of the cell is determined to increase.

5. The method of claim 1, further comprising, after step (d), a step of determining the test substance to be an agent that inhibits the tyrosinase gene expression, when the pigmentation of the cell is determined to decrease.

6. A method for whitening skin of a subject, comprising administering a composition comprising a miRNA of SEQ ID NO: 1 as an active ingredient.

7. The method of claim 6, wherein the composition is applied externally to skin of the subject.

8. The method of claim 6, wherein the composition is administered into the subject.

9. A method for preventing gray hair of a subject, comprising administering a composition comprising, as an active ingredient, an antisense nucleic acid molecule of SEQ ID NO: 2, which has a nucleotide sequence complementary to a miRNA of SEQ ID NO: 1 and is capable of hybridizing to the miRNA.

10. The method of claim 9, wherein the composition is applied externally to skin of the subject.

11. The method of claim 9, wherein the composition is administered into the subject.

* * * * *